United States Patent [19]

Sulek et al.

[11] Patent Number: 5,487,740
[45] Date of Patent: Jan. 30, 1996

[54] LASER DEVICE FOR ABLATION OF HUMAN TISSUE

[75] Inventors: Stanislaw Sulek, Irvine; Hany M. G. Hussein, Newport Beach, both of Calif.

[73] Assignee: Energy Life Systems Corporation, Costa Mesa, Calif.

[21] Appl. No.: 204,980

[22] Filed: Mar. 2, 1994

[51] Int. Cl.$^6$ .................................................. A61B 17/36
[52] U.S. Cl. .............................................. 606/15; 606/17
[58] Field of Search ................................. 606/15, 16, 17, 606/7, 13, 14, 18

[56] References Cited

U.S. PATENT DOCUMENTS

| | | |
|---|---|---|
| 4,461,283 | 7/1984 | Doi . |
| 4,646,737 | 3/1987 | Hussein et al. . |
| 4,740,047 | 4/1988 | Abe et al. . |
| 4,950,267 | 8/1990 | Ishihara et al. . |
| 5,188,634 | 2/1993 | Hussein et al. . |
| 5,190,538 | 3/1993 | Hussein et al. . |
| 5,242,437 | 9/1993 | Everett et al. ............................ 606/15 |
| 5,242,438 | 9/1993 | Saadatmanesh et al. ................ 606/15 |
| 5,322,507 | 6/1994 | Costello et al. .......................... 606/17 |

FOREIGN PATENT DOCUMENTS 0073617  3/1983  European Pat. Off. ................ 606/15

OTHER PUBLICATIONS

Histopathological Changes occuring in the prostrate following laser prostatectomy, Johnson, D. E. et al, Poroceedings of Biomedical Optics '91, vol. 1421, 1921—4 pages.

Pathologic Changes Occurring in the Prostate Following Transurethral Laser Prostatectomy, Douglas E. Johnson et al, Lasers In Surgery and Medicine 12:254–263 (1992).

*Primary Examiner*—Stephen C. Pellegrino
*Assistant Examiner*—Sonya Harris-Ogugua
*Attorney, Agent, or Firm*—James G. O'Neill

[57] ABSTRACT

A medical device and method are provided for generating deep coagulation necrosis as well as surface vaporization in the site of a body cavity. The device provides means for delivering laser energy from the side of the device while providing localized irrigation at its laser delivery port. Laser energy is delivered from a fiberoptic that is bent at its distal end and placed in a catheter body which includes an irrigation channel that terminates at the distal end of that fiberoptic. Deep coagulation necrosis is achieved by: a) placement under endoscopic guidance of the device in the body cavity, b) delivering a predetermined dose of laser energy to target tissue, and c) rotating the device continuously during laser delivery, with at least one revolution in one direction. After the coagulation session has been completed, a detachable heat-generating cap may be mounted at the distal end of the catheter in order to convert the direct laser energy into controlled thermal energy at the surface of that cap. Placement of the heated cap in contact with tissue causes localized and efficient vaporization of that tissue and subsequently creates an immediate lumen within the tissue.

19 Claims, 14 Drawing Sheets

LASER DEVICE FOR ABLATION OF HUMAN TISSUE

TECHNICAL FIELD

This invention relates generally to laser catheters, and more particularly to catheters suitable for the laser ablation in vivo of human tissue, such as for the treatment of Benign Prostatic Hyperplasia (BPH) and prostate cancer.

BACKGROUND ART

Today, Trans Urethral Resection of the Prostate (TURP) is the standard therapy for Benign Prostatic Hyperplasia (BPH) and prostate cancer. TURP employs an electrosurgery device and resectoscope for the surgical removal of prostatic tissue through the urethra. Approximately 400,000 prostatectomies are performed annually in the United States at a cost of nearly five billion dollars. Immediate postoperative morbidity is about 18% for this procedure. TURP generally requires 5 days of hospitalization and 6 weeks for recovery. Complications of TURP include blood loss, impotence, and incontinence. The high cost of TURP and its associated morbidity have given urologists a strong incentive to seek alternate therapies for BPH. Alternative new technologies are being developed as minimally invasive means for the treatment of BPH. These technologies include lasers, microwave, ultrasound. stents, balloon dilatation, and drugs.

MERCK's Proscar™, a drug approved in 1992, requires more than six months to produce a therapeutic effect and is limited in its utility to probably 25% of BPH patients. Balloon dilatation products have been on the market for several years but have proven unsuccessful.

Stents being developed for the treatment of BPH are undergoing clinical trails. The initial clinical results demonstrate the incidence of significant complications, such as stent migration and increased frequency of urination. Ultrasound ablation and microwave have demonstrated a lesser degree of improvement in patient symptoms when compared to TURP.

Laser ablation offers a viable alternative to TURP and other therapeutic modalities for the treatment of BPH. Laser ablation provides means for achieving deep and controlled depth of penetration of laser energy into prostatic tissue. Thus, a large volume of the diseased prostate can be ablated without causing damage to surrounding tissues.

Clinical results from a prospective randomized clinical trail of laser ablation compared to TURP were presented at the 1993 meeting of the American Urological Association (AUA). These results indicate that laser ablation is comparable to TURP in terms of the improvement in urinary flow rate and symptom scores, but is superior to TURP with respect to the risk of impotence and blood loss. A very significant advantage of laser ablation is the cost effectiveness of this procedure. When compared to TURP, Laser ablation was shown to shorten the time for return to normal activity from 6 weeks to 1 week; shorten hospital stay from 3.2 days to 1.6 days; and shorten intraoperative time from 22 minutes to 12 minutes.

Nd:YAG lasers are the energy source of choice for this procedure. These lasers operate at the near infrared zone of the spectrum at a wave length of 1.06 micrometers. This wave length is known to have a very high scattering coefficient in water and soft tissue, and accordingly an ability to penetrate deep into the tissue without being absorbed at the surface. Laser energy causes thermal coagulation necrosis which results in tissue absorption and sloughing within four weeks from the laser treatment.

Nd:YAG lasers are solid state user-friendly systems that have been used in hospitals and approved by the FDA for nearly 15 years. It is estimated that there is an installed base of over 2,000 Nd:YAG lasers in U.S. hospitals today. Many of these lasers can provide the energy required for laser ablation of the prostate.

Commercially available laser catheters such as those marketed by C. R. Bard and Myriadlase utilize a metal reflector for diverting the laser beam into a lateral direction (U.S. Pat. No. 5,242,437-Everett et al). These catheters have a tendency to overheat at the catheter tip, which could lead to tip detachment during clinical use, thus raising a serious safety concern. Other commercial laser catheters such as those marketed by Laserscope and Heraeus Surgical employ the principle of Total Internal Reflection (TIR) at the distal end of the fiberoptic by providing a beveled surface at the tip of the fiber or adding a prism to that fiber (i.e., U.S. Pat. No. 4,740,047-Abe et al). These surfaces or prisms cause the laser beam to exit from the side of the fiberoptic. These catheters also experience overheating and unpredictable performance. It is, therefore, desirable to have a fiberoptic delivery system that provides the means for safe and effective transfer of the laser energy to specific area of the patient being operated on.

The present invention solves the above set forth problems and meets the foregoing desires by the provision of means and methods for the ablation of prostatic tissue in a living human by subjecting the prostate, at a selected site, to a laser beam having sufficient power, and for a sufficient time to create a deep lesion at such site. The site be treated can be identified and monitored by endoscopic examination during the time of laser ablation. Delivery of the laser energy from the side of the catheter is accomplished without the use of reflector surfaces, prisms, or beveled surfaces, thus solving the problem of heat generation, which can cause device failure and unpredictable performance. Furthermore, the laser energy can be emitted continuously with the method disclosed herein since the catheter is rotated in an at least one direction, and preferably in an oscillatory manner, in both the clockwise and counter clockwise directions. This rotational method prevents localized overheating of the tissue by allowing adequate time for the tissue near the surface of the urethra which has been treated to cool down while the laser energy is applied to adjacent sites. This rotational method, therefore, prevents subsurface ablation ("popcorn effect") and subsequent bleeding, which is a common clinical complication in today's laser ablation of the prostate. Localized irrigation is provided at the tip of the catheter to help maintain the laser output and assist in cooling the surface of the prostatic urethra during laser delivery.

It would also be desirable to have a device and method for vaporizing prostatic tissue following the laser coagulation procedure in order to create a definitive lumen that can facilitate urination and eliminate the need for placing a urinary drainage catheter. Currently, laser coagulation of the prostate causes edema (swelling) of the prostate at the treatment site. As a result, the treated tissue obstructs the urethra and makes it difficult for the patient to urinate.

The present invention satisfies the foregoing desires by providing means and method for vaporization of prostatic tissue as the sole therapy, or as an adjunct to laser coagulation or other interventional procedures, such as microwave therapy.

DISCLOSURE OF THE INVENTION

The present invention provides a fiberoptic laser ablation catheter capable of generating large coagulative necrosis lesions in the prostate while providing a definitive lumen through the urethra for the immediate relief of symptoms. This inventive device is used under endoscopic control, thus providing a minimally invasive procedure for the treatment of prostate disorders.

The catheter of the present invention eliminates the need for a reflector, prism, or other components at the distal end of the fiberoptic thus minimizing the potential for overheating at the catheter tip. Deflection of the laser beam to the side of the distal tip of this catheter is accomplished by bending the tip of the fiberoptic to a prescribed angle. The bent tip of the fiberoptic terminates at an aperture placed on the side of the catheter tip, in order to permit side-firing of the laser catheter when activated. The use of the bend increases the divergence angle of the laser beam thus increasing the spot size of this beam at the surface of the tissue. This in turn allows deep penetration of laser energy into tissue with minimal vaporization of this tissue at the surface. The maximum limit of the divergence angle is increased by the utility of a fiberoptic having a high numerical aperture. At least one fiberoptic is provided within the catheter and is situated to direct a laser beam at a tissue target site that is adjacent to the side wall of the catheter tip.

An integral irrigation channel is provided in the present invention, in order to provide means for localized irrigation at the distal end of the fiberoptic. This helps maintain the power output and the integrity of the laser catheter, and minimizes the required volume of the irrigation fluid. When compared to other laser delivery systems that rely on excessive irrigation of the urethra through an endoscope, the present invention solves the problem of overloading the bladder.

The present invention also provides a method for delivering the desired laser energy while the laser catheter is being rotated in at least one direction, but preferably in an oscillatory manner from its initial position; such oscillatory rotation is in both the clockwise and counter clockwise directions. This method prevents explosive tissue effects and subsequent bleeding, that is common with prior art devices and methods.

Additional improvement is achieved by the placement at the tip of the laser catheter of a detachable metal cap which covers the distal end of the fiberoptic and the irrigation port. Upon delivery of laser energy, this cap absorbs the delivered energy and generates heat. Therefore, when brought in contact with prostatic tissue, the heated metal cap conducts heat to this tissue causing localized vaporization of the tissue. A thermocouple is attached to or contacts the metal cap in order to monitor and control its surface temperature during use. Continuous fluid irrigation is provided in the space between the outer surface of the catheter tip and the inner surface of the metal cap. This irrigation helps to prevent overheating of the laser catheter tip. The addition of the metal cap allows this device to generate a definitive lumen in the prostatic urethra following the direct delivery of the laser energy to the prostate, which results in the formation of a deep coagulative lesion. The generation of a definitive lumen should facilitate urination and eliminate the need for placement in the patient of a urinary drainage catheter following the laser procedure for prostatic tissue coagulation.

A significant cost advantage is realized by converting the same laser catheter that was used in a given patient to produce tissue coagulation, into a vaporization device. Prior art devices such as those marketed by C. R. Bard and Myriadlase are used to create tissue coagulation, while vaporization of tissue in the same patient is accomplished by using a second device, such as the sapphire-tipped contact laser fiber marketed by Surgical Laser Technologies. The use in the same patient of these two disposable devices increases the cost of the procedure and is, therefore, undesirable in today's environment, which demands cost-effective therapy.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, wherein:

BEST MODES FOR CARRYING OUT THE INVENTION

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide for improved and novel devices and methods for the laser ablation in vivo of prostatic tissue.

Figure 1:
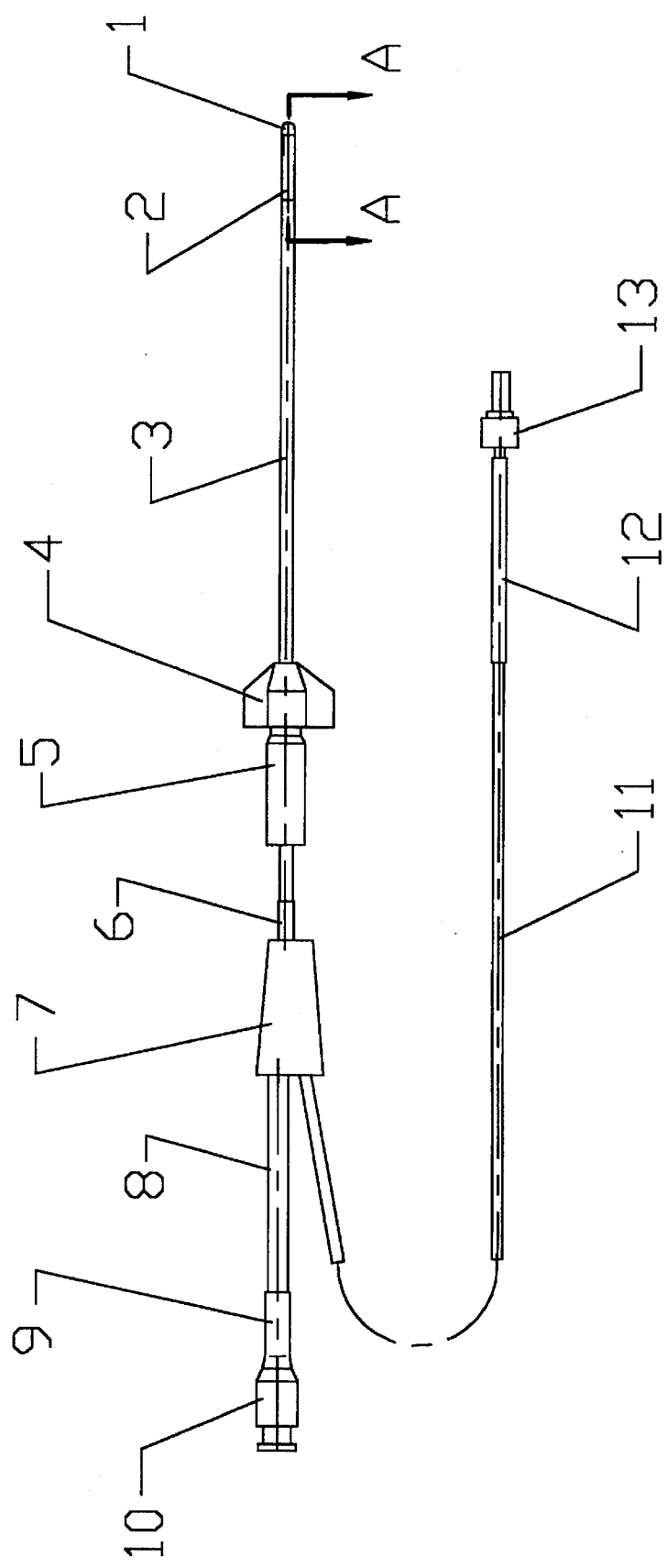
FIG. 1 is a top plan view of a laser ablation catheter in accordance with the present invention.

Referring now to FIG. 1, a first embodiment of a laser ablation catheter, in accordance with the present invention is shown as including a tubular catheter body 3 having a distal tip 1, a distal housing 2, a nut handle 4, a nut body 5, a strain relief 6, a Y connector 7, an irrigation tubing 8, a further strain relief 9, a Luer Lock™ 10, a tubing 11 having a fiberoptic therein, a strain relief 12, and a fiberoptic connector 13.

Figure 2:
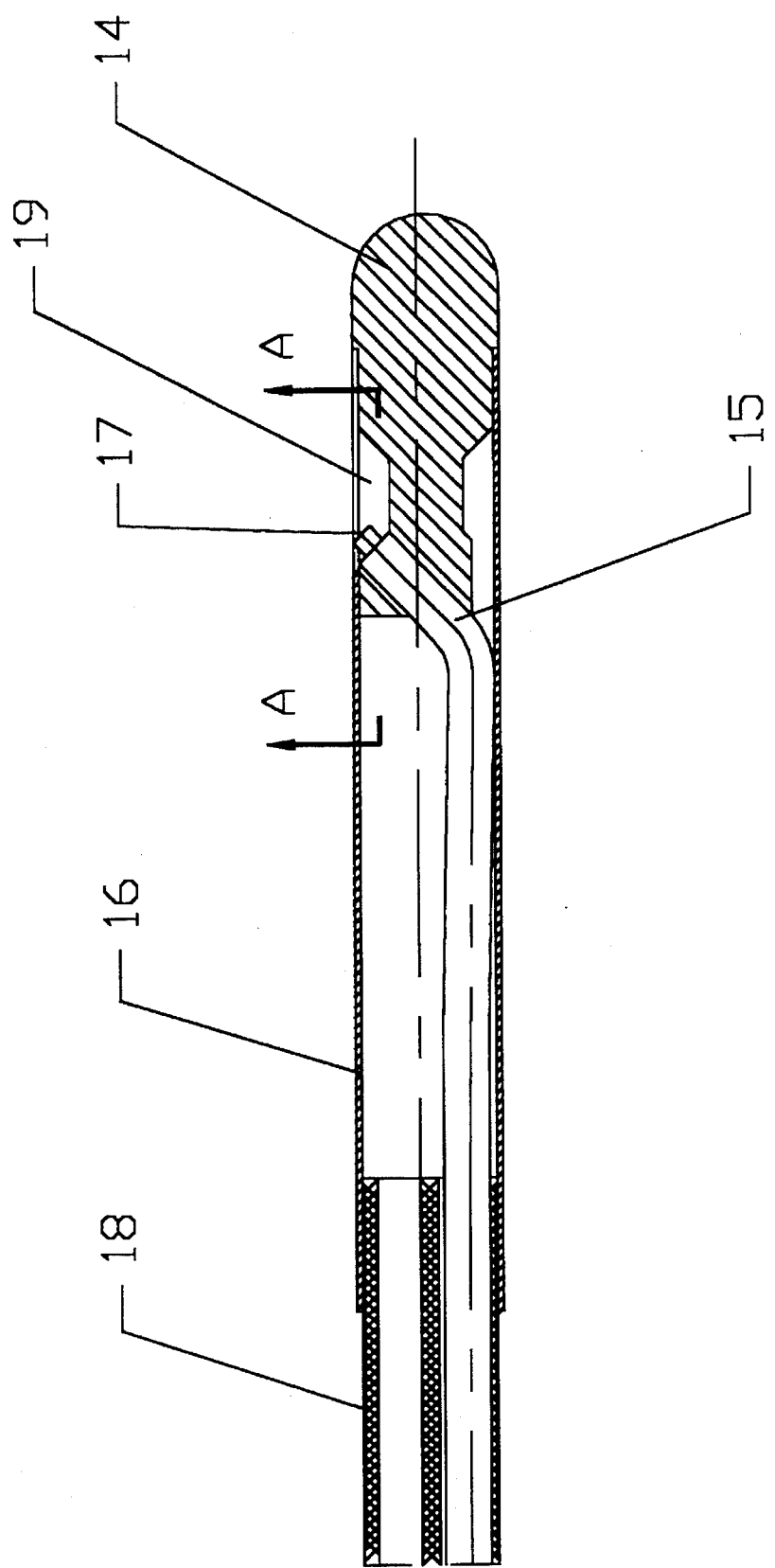
FIG. 2 is an enlarged cross-sectional view of the distal end region of the catheter, taken along line 2—2 of FIG. 1.
Figure 3:
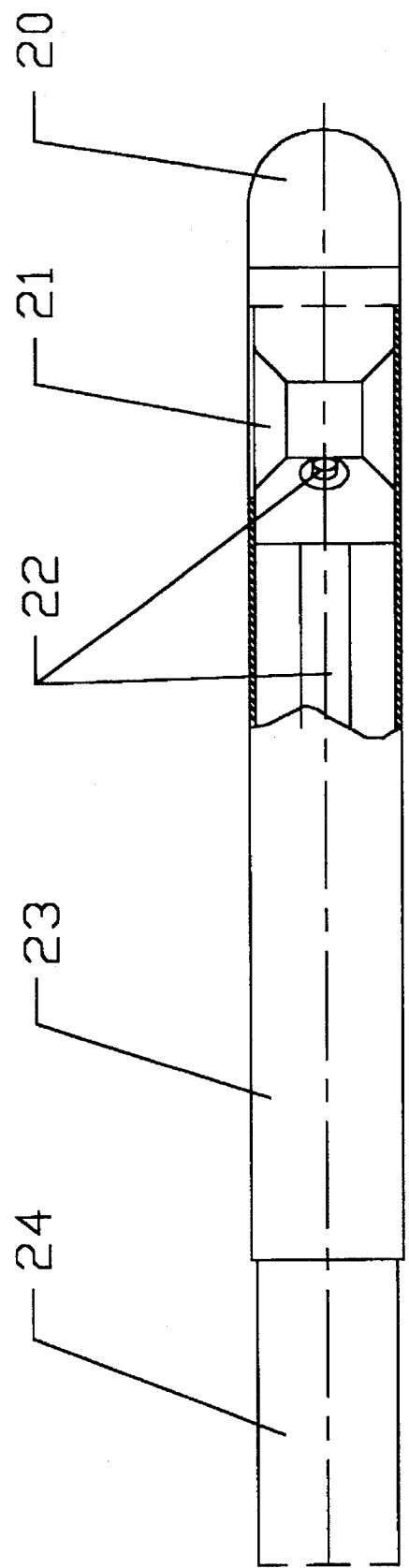
FIG. 3 is a further cross-sectional view of the distal end region of the catheter, taken along line 3—3 of FIG. 2.

Turning now to FIGS. 2 and 3, FIG. 2 shows an enlarged cross-section of the catheter of FIG. 1 taken along line 2—2, at the plane of the fiberoptic axis of the distal end region. This FIG. 2 shows the distal housing 2 as having the distal tip 1, a fiberoptic 15 with one or more fibers or fiber bundles therein, a laser aperture 17, the catheter tubing 3 and at least one side port 19, preferably placed at a distance, such as at least 1 millimeter, from the distal end of the catheter. The side port 19 is in fluid communication with an irrigation channel or lumen 20. While FIG. 3 shows still another enlarged cross-section of the distal end region, taken along line 3—3 of FIG. 2.

Figure 4:
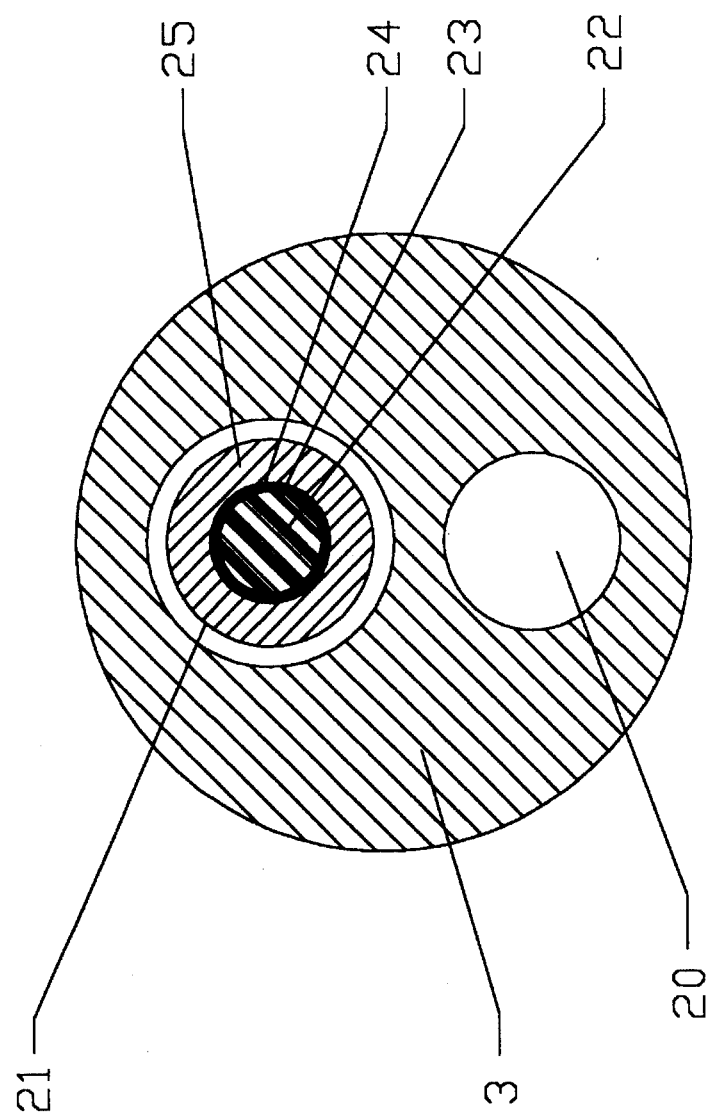
FIG. 4 is an enlarged cross-sectional view of the body of the laser ablation catheter, taken along line 4—4 of FIG. 3.

FIG. 4, shows a cross-section of the catheter tubing 3 containing two separate lumens; the first being the irrigation lumen 20, and a second lumen 21, for containing and protecting the fiberoptic 15. This FIG. 4 also shows a detailed cross-section of the fiberoptic 15, including a fiberoptic core 22, a primary cladding 23, a secondary cladding 24, and a buffer 25. Each of the primary and secondary claddings are made from materials which are selected so as to have an index of refraction that is significantly lower than that of the fiberoptic core material.

Figure 5:
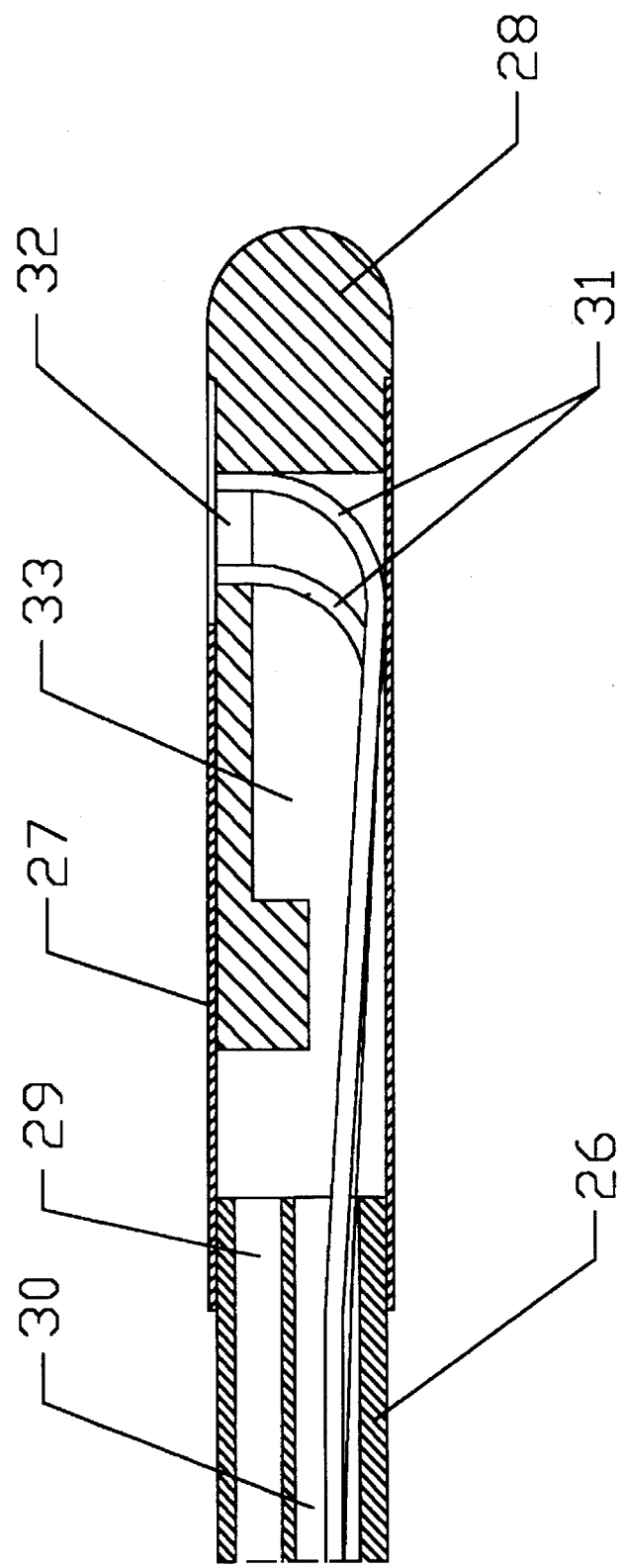
FIG. 5 is an enlarged cross-sectional view of the distal end region of a further embodiment of the laser catheter of the present invention.

An alternate catheter design is shown in FIG. 5 where the distal end region is provided with a fiberoptic bundle 31 which contains multiple fiberoptics. A catheter tubing 26 contains an irrigation channel 29 and a fiberoptic channel 30. The irrigation channel 29 is in fluid communication with an irrigation chamber 33, which irrigation chamber 33 terminates in and is fluidly connected to a side port 32, located in a distal tip 28. The distal housing 27 terminates at its distal end in the distal tip 28.

The size of the lasing catheter of the present invention can vary in the range of from about 3 French (1 millimeter) to about 12 French (4 millimeters). Preferably, a preferred embodiment of a laser catheter of the present invention has a diameter of about 7.5 French (2.5 millimeters).

The size of the fiberoptic inside a catheter of the present invention can also vary. If a single fiber optic is used the core diameter can vary from about 250 micrometers to about 500 micrometers. A preferred embodiment of the laser catheter of the present invention employs a fiberoptic having a core diameter of approximately 365 micrometers. If a multi-fiber bundle is used, individual optical fibers having a core diameter in the range of from 30 to 200 micrometers can be used.

The bend of the end or tip of the fiberoptic in the catheter, which defines the launching angle of the laser beam into the tissue, can vary from about 20° to about 90° with respect to the central axis of the catheter. A preferred embodiment of the laser catheter of the present invention has a launching angle of about 45°. This angle is helpful in keeping away from the laser aperture (side port), any tissue debris that may be ejected from the prostate during an operation. Preferably, the divergence angle of the laser beam exiting from the fiberoptic approaches the acceptance angle of the fiber used.

Several types of lasers may be utilized for the ablation of the prostate by means of the laser catheter of the present invention. The choice of a particular wavelength is influenced in part by the desired depth of penetration in prostatic tissue. Treatment of Benign Prostatic Hyperplasia (BPH) by laser ablation relies primarily on causing irreversible damage to a large volume of prostatic tissue so as to cause sloughing of that tissue over a period of 4 to 6 weeks following the treatment. Typically effective ablation of the prostate requires immediate generation of a spherical zone of tissue necrosis having a diameter of approximately 2.6 centimeters in tissue model. In order to affect the prostatic tissue that is situated that far beneath the urethral surface the requirement exists for a laser wavelength that has a very low absorption coefficient and very high scattering coefficient in the tissue. These characteristics are met by the Neodymium-doped Yttrium-Aluminum-Garnet (Nd:YAG) laser which operates at the wavelength of 1.06 micrometers in the near-infrared zone of the spectrum. This is a continuous wave solid state laser capable of generating high powers (typically 40–100 Watts) in a compact portable package, thus making this laser practical for surgical use. This wavelength is readily transmissible through standard fiberoptics. These advantages make the Nd:YAG laser the preferred energy source for the laser catheter of the present invention. Other appropriate wavelengths may also be utilized. Diode lasers operating in the wavelength of 700 to 1000 nanometers may also be appropriate for this application, while offering advantages in the size, convenience, and cost when compared to Nd:YAG lasers. The use of dual wave length lasers (e.g. 1064/532 nanometers) may be desirable for creating combined coagulation and surface vaporization. Pulsed as well as continuous wave lasers can be employed.

For ablation of prostatic tissue the energy parameters are determined from a dosimetry study that identifies the requirements of laser power, exposure time, number of applications, and other pertinent parameters such as the minimum flow rate of the irrigation fluid. The laser power requirement is typically in the range of 15 to 60 Watts at the tissue, and the exposure time is in the range of 4 to 12 minutes. The laser catheter of the present invention preferably utilizes 40 Watts delivered for four minutes.

Prior art devices for laser ablation of prostatic tissue, such as these marketed by C. R. BARD and Myriadlase, employ water at flow rates that could exceed 300 cubic centimeters per minute, for the irrigation of these devices. While such high flow rates are necessary to maintain the distal end of these devices at low temperature, excessive irrigation volume requires frequent drainage of urine from the patient, thus causing unnecessary interruption to the surgery. The laser catheter of the present invention has a dedicated integral irrigation channel that provides localized delivery of the irrigant fluid at the side port of this catheter, adjacent the tip of the laser fiber. This irrigation system provides efficient means of irrigation to support the operation of the catheter. Typical flow rates required in this catheter are in the range of 2 to 20 Cubic centimeters per minute.

A prior method of energy delivery developed by Douglas E. Johnson at the University of Texas M. D. Anderson Cancer Center, Houston, Texas, requires laser delivery for a certain period of time (e.g., 60 seconds) at a given quadrant (e.g., the 12 o'clock position), and the repeated delivery of this energy at the three other quadrants. While this method is effective, it would be desirable to develop an alternate method that requires less attention from the user while producing a more uniform ablation zone in the tissue, and avoiding overheating of tissue surface and subsequent subsurface ablation (or Popcorn effect), that typically results in bleeding during the procedure. The present invention satisfies this requirement by permitting continuous laser delivery while the catheter is preferably rotated a full turn in the clockwise direction to be followed by another full turn in the counter clockwise direction. The catheter may also be slowly rotated in only one direction, if desired. Any such rotation, particularly in an oscillatory fashion may be done either manually, or by using a motor drive operating in the range of from 0.3 to 100 revolutions per minute. A range of rotational speeds of 1 revolution per minute to 1 revolution per second was tested in tissue model and was shown to produce uniform and equal zones of thermal necrosis having a diameter of approximately 2.9 centimeters. Furthermore, animal studies demonstrate that 40 Watts of laser power delivered for 4 minutes using this rotational method can produce a zone of thermal necrosis having a diameter of approximately 2.6 centimeters in a dog's prostate. The prior art quadrant method requires 60 Watts for 4 minutes, or 50% more energy, in order to produce the same tissue effect.

Figure 6:
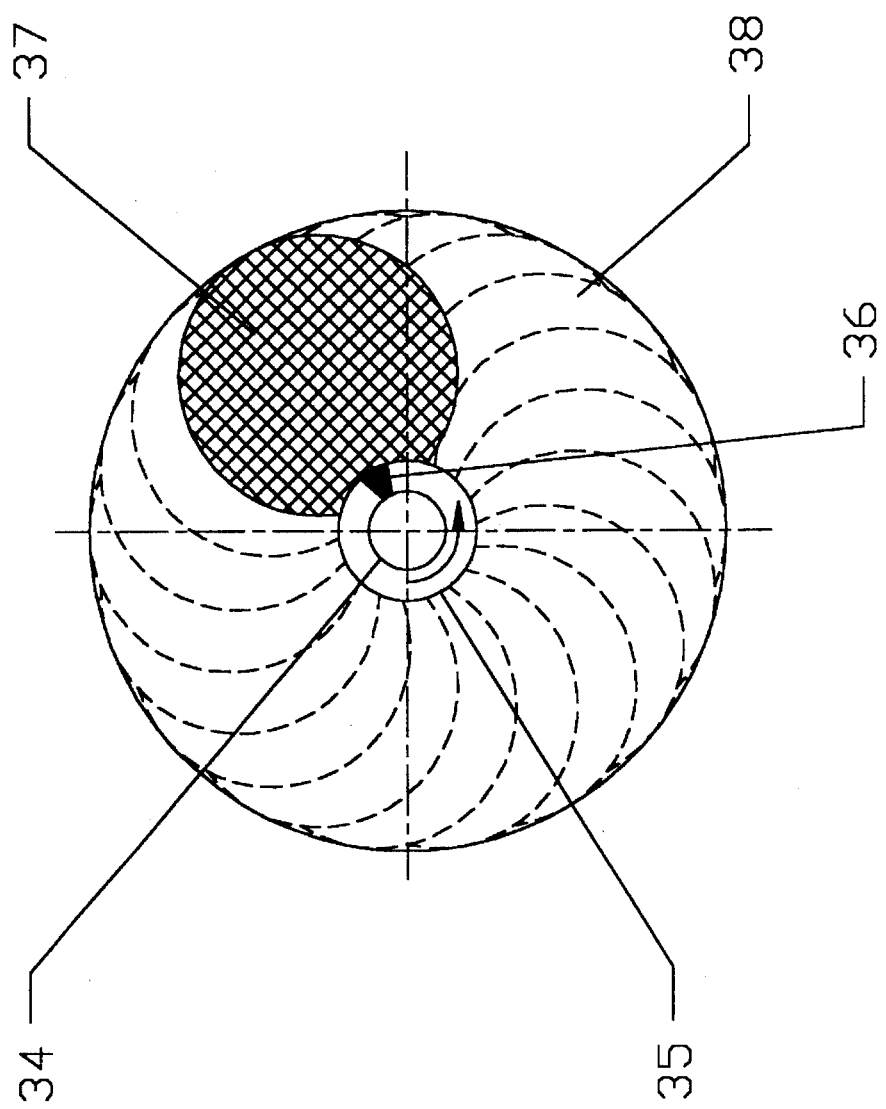
FIG. 6 is a schematic illustration of the rotational method for laser ablation of a prostate in accordance with the present invention.

FIG. 6 demonstrates the rotational method of the present invention for laser ablation of the prostate. In this figure, a laser catheter 34 of the present invention is placed in a prostatic urethra 35. A laser beam 36 is emitted from a bent fiberoptic through a side port of the laser catheter. A single lesion 37 can be generated if the laser catheter is held stationary during laser delivery. A continuous zone of coagulation 38 is generated if the catheter is rotated clockwise and then counterclockwise, during laser delivery.

Figure 7:
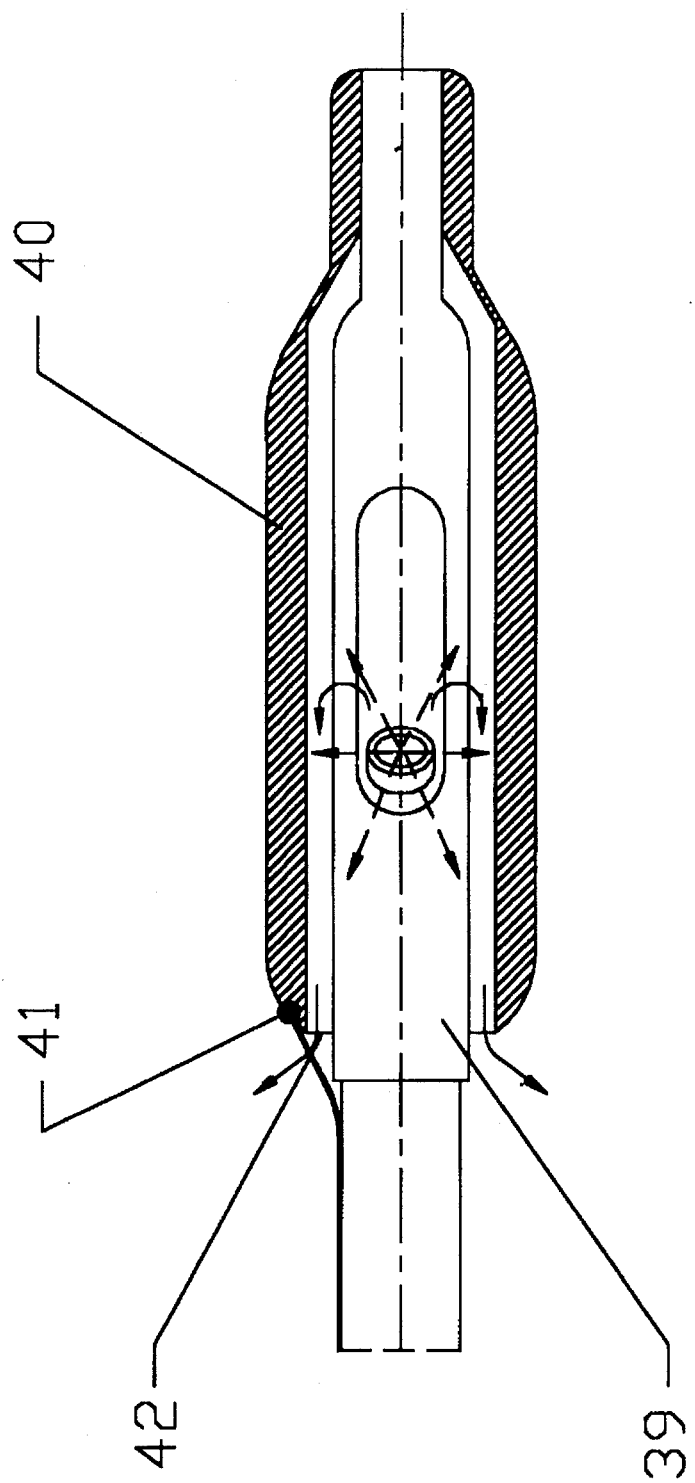
FIG. 7 is an enlarged cross-sectional view of the distal end of a laser catheter of the present invention, modified to incorporate a detachable metal cap thereon.

FIG. 7 shows a modified laser catheter for combined coagulation and vaporization of tissue. A catheter 39, similar to the catheter shown in FIGS. 2 and 3, or the catheter shown in FIG. 5, has a detachable cap 40, made from any suitable material, such as stainless steel, mounted by an operator over a distal end 43 of the catheter, following the coagulation procedure. This added cap converts the catheter 39 into a vaporization device that can create an immediate channel in the treated tissue. The desirable outer diameter of the cap 40 is in the range of from 3 to 10 millimeters. The feasibility of employing a detachable stainless steel cap having an outer diameter of 5 millimeters was demonstrated in a tissue model. It was shown that approximately 40 Watts of laser power is required to cause tissue vaporization when using this cap. A thermally-insulating sleeve (e.g. glass) may be made an integral part to the added cap 40. A thermocouple 41 is attached to the cap in order to monitor the cap temperature. This thermocouple can be connected to the laser energy source to provide a closed loop feedback control system that maintains the cap temperature at the desired level. Irrigation fluid 42 is delivered by the laser catheter through a side opening therein, to prevent this catheter from overheating during laser delivery.

Figure 8:
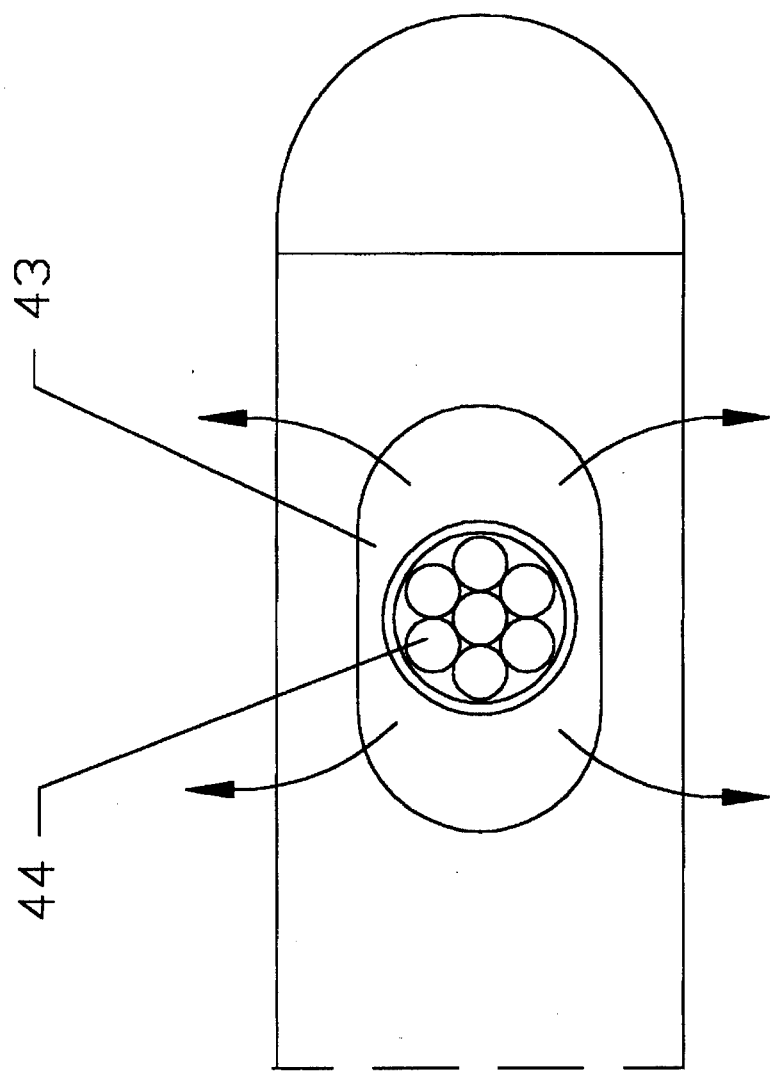
FIG. 8 is an enlarged end view showing an irrigation port surrounding a plurality of fiberoptics.

FIG. 8 is a top view of the distal end region of the catheter of FIG. 8 and shows a fiberoptic bundle 44 surrounded by an irrigation port 43.

Figure 9:
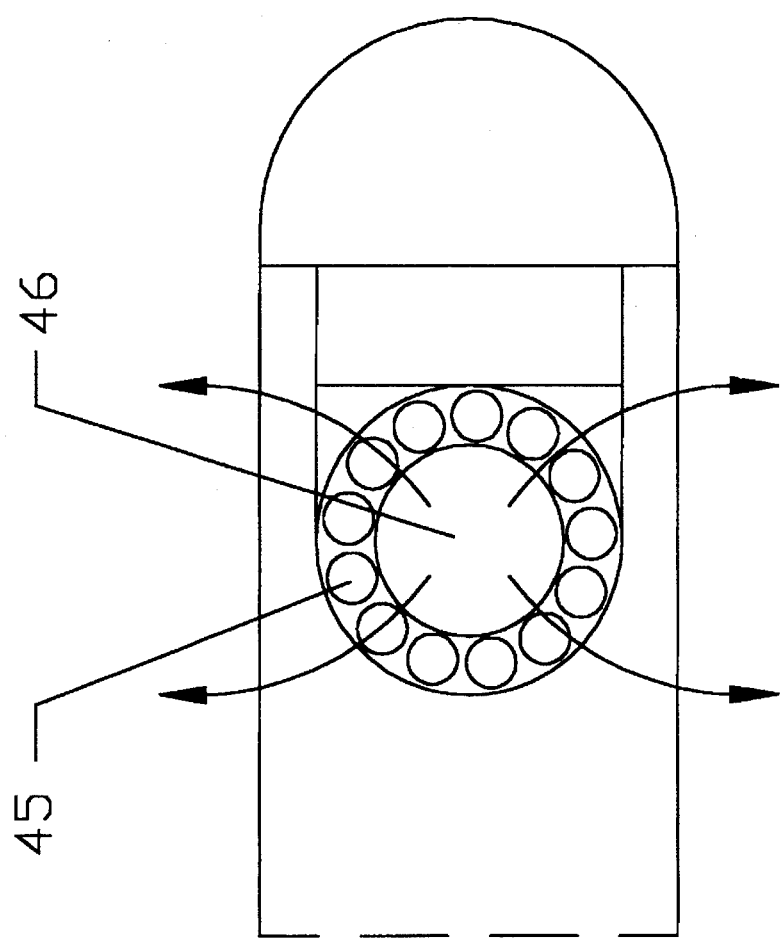
FIG. 9 is an enlarged end view showing a plurality of fiberoptics surrounding an irrigation port.

FIG. 9 is a further top view of the distal end region of an alternate configuration of the catheter of FIG. 15 showing a multiple fiberoptic bundle 45 surrounding an irrigation port 46.

Figure 10:
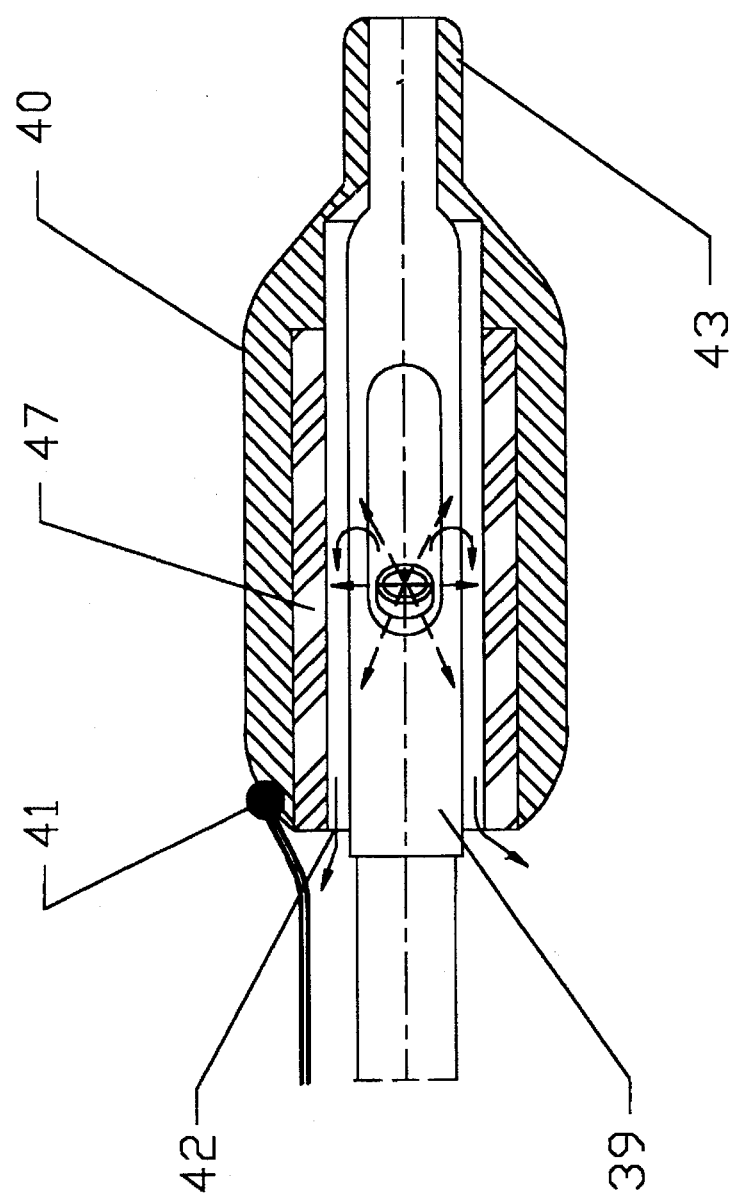
FIG. 10 is an enlarged cross sectional view of the distal end of a laser catheter of the present invention showing a glass insert and a thermocouple attached to the heat generating element or cap.
Figure 11:
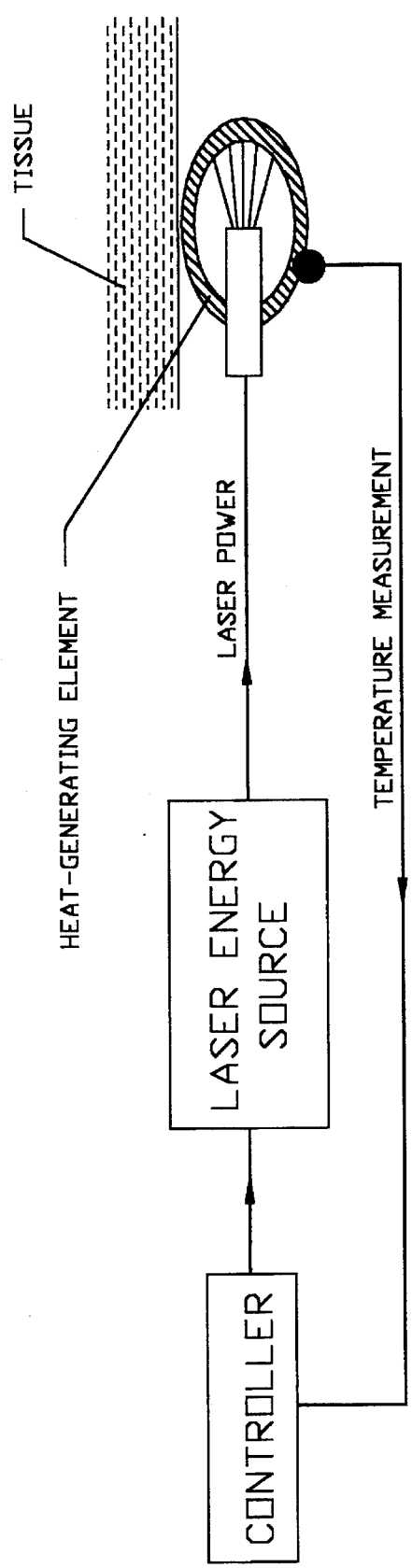
FIG. 11 is a block diagram of a closed-loop feedback control system that can be employed for controlling the temperature of the heat generating element mounted at the distal of the fiberoptic of the present invention.

FIG. 10 illustrates a cross section of the distal end of the lasing catheter having a heat generating element or cap 40, an inner lining 47 that transmits laser energy and provides thermal insulation, and a thermocouple 41 attached thereto, for monitoring and controlling the temperature of the heat generating cap. While FIG. 11 illustrates a block diagram of one embodiment of a close-loop feedback control system that employs the measurement of heat generating cap temperature to adjust the output power of the laser energy source in order to maintain the heat generating cap at a constant temperature.

Figure 12A:
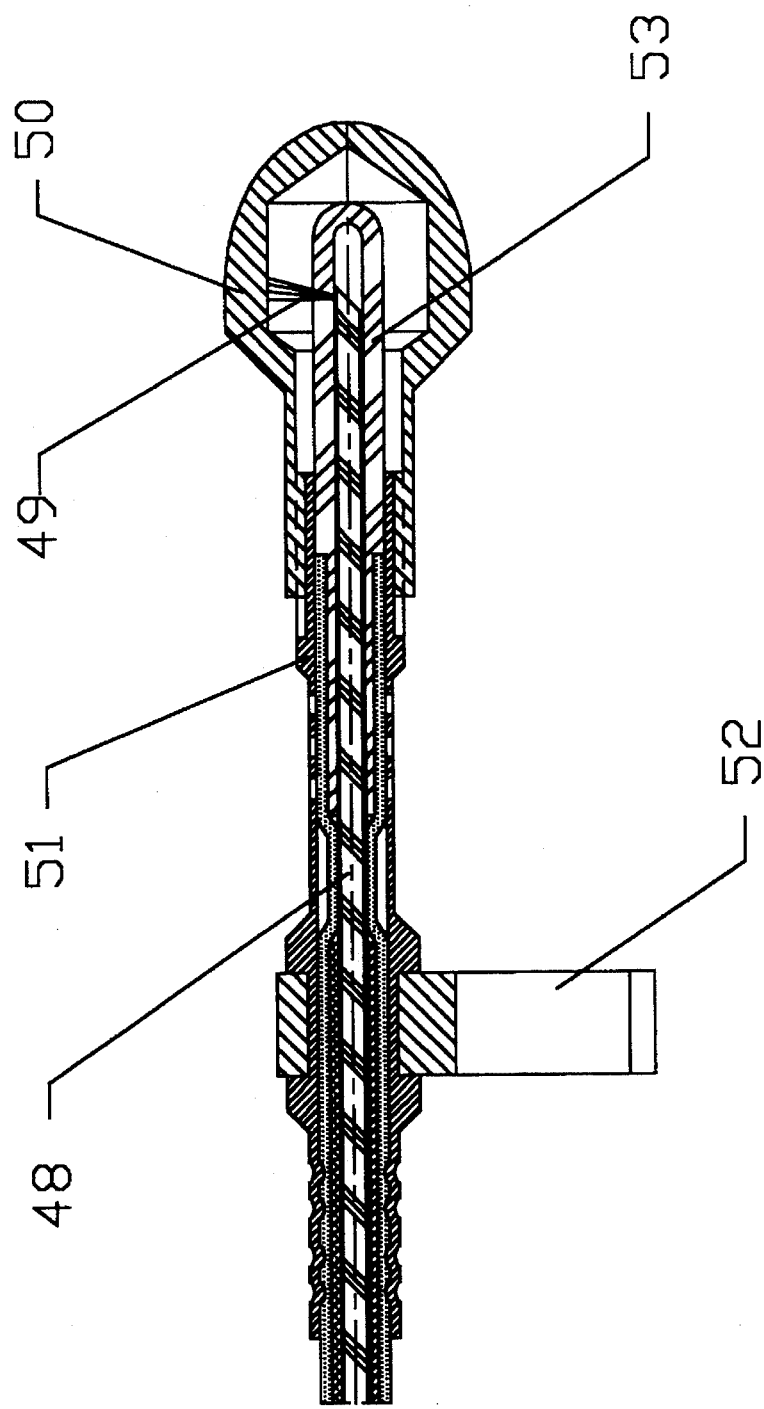
FIGS. 12A, 12B and 13 show various embodiments of the heat generating element or cap mounted to the distal end of the present invention.
Figure 12B:
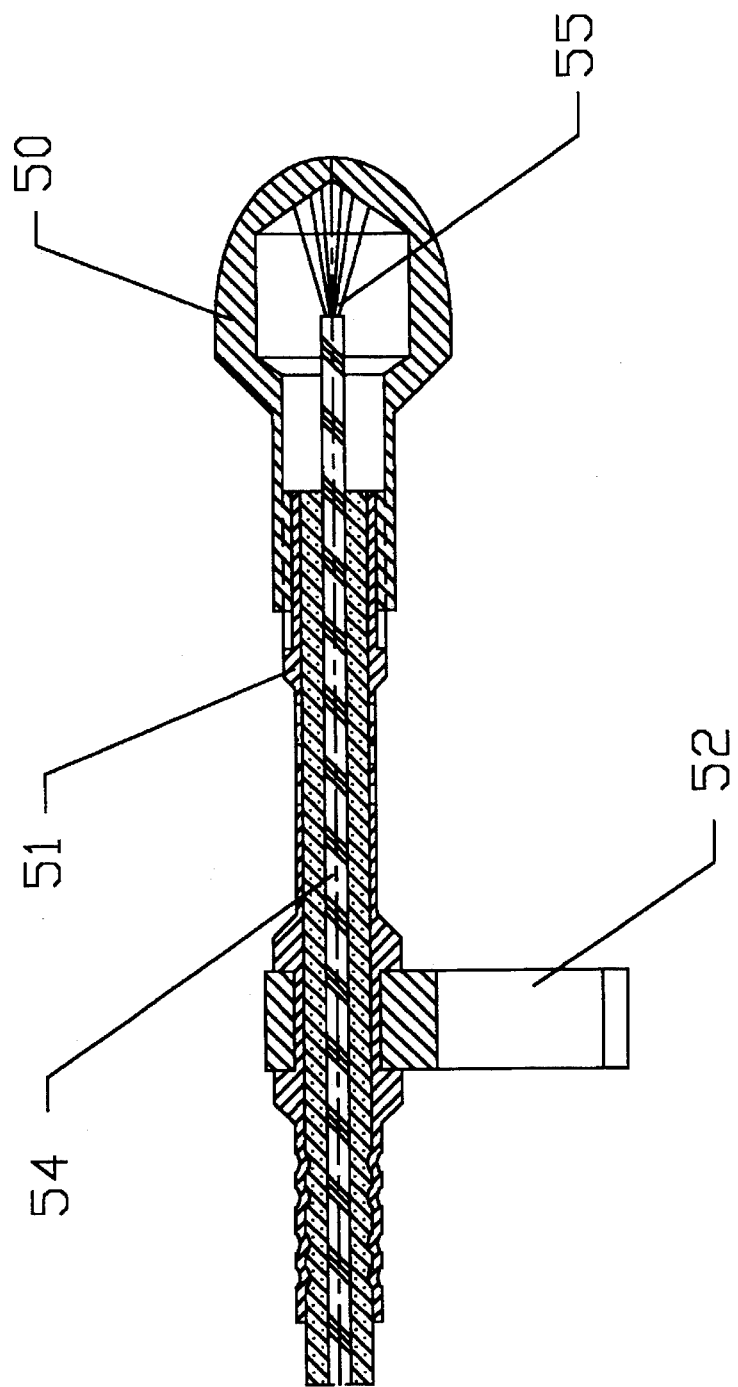

FIGS. 12A and 12B show cross sections of further preferred embodiments of the device of the present invention having a larger or enlarged cap, such as in the 10 mm. range referenced above. In particular, FIG. 12A includes a catheter having at least one fiberoptic 48 terminating in a beveled portion at its distal end, for directing laser energy into a laser port aperture 49, for delivering laser energy laterally from the fiberoptic. A heat generating element or cap 50 is mounted at the distal end of the catheter around the fiberoptic so as to receive the laser energy delivered from the laser port and to convert this energy into heat. The heat generating element or cap 50 may include a metal sleeve 51 secured to the distal end of the catheter so as to allow the heating element 50 to be permanently or removably mounted on the catheter. An attachment 52 may be anchored to the catheter distal end to facilitate mounting the catheter on the moving element of an appropriate endoscope, (e.g., Iglesias style). Preferably a glass housing 53 surrounds the distal end of the fiberoptic 48.

FIG. 12B shows a still further embodiment having a catheter with at least one fiberoptic 54 having a straight distal end and a laser aperture 55 that permits the laser beam to exit from the fiber in a forward direction, so as to impinge upon the inner surface of the heat generating element or cap 50.

Figure 13:
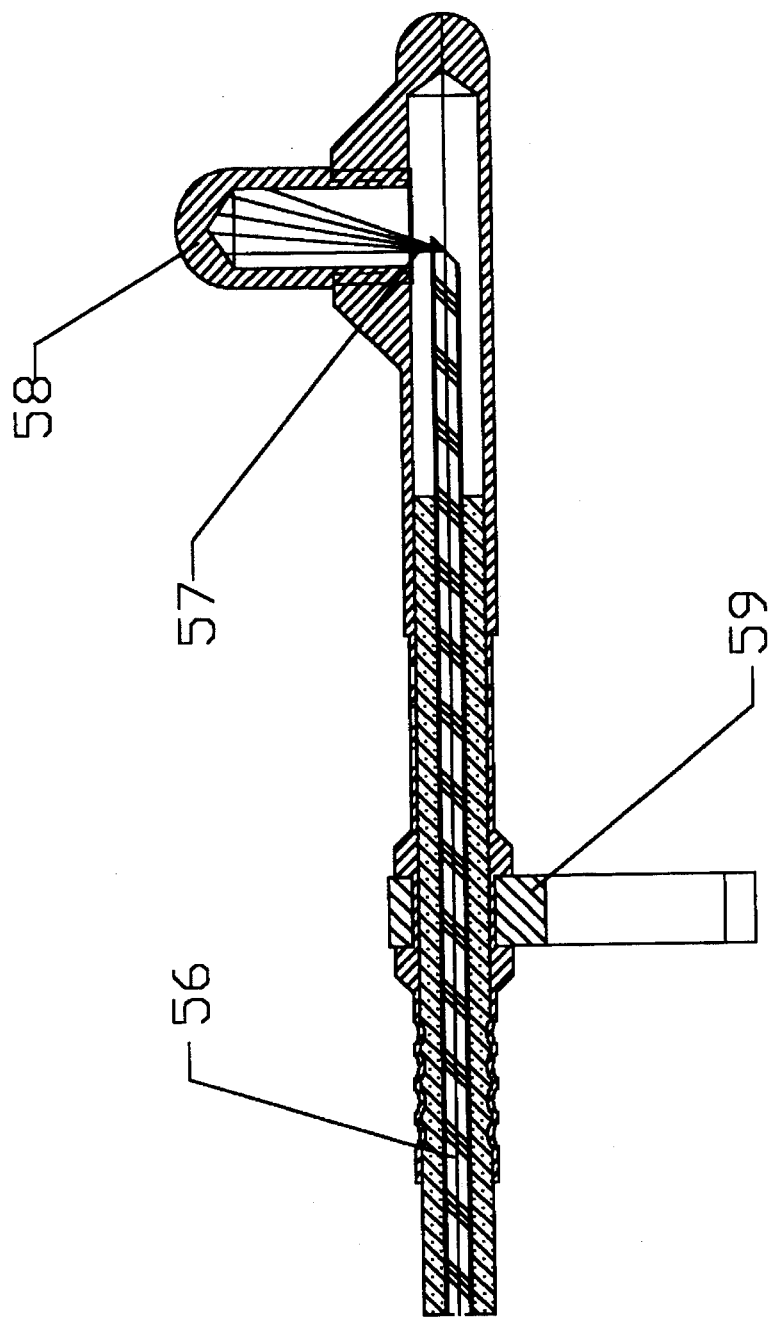

FIG. 13 is a cross sectional view of a still further embodiment of the distal end region of the catheter of the present invention showing a fiberoptic 56 that terminates in a beveled portion at its distal end for directing laser energy into a laser port 57 where the laser energy impinges on a heat generating element or cap 48 that is mounted laterally to the end of the catheter.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A lasing catheter for laser ablation of human tissue in a selected body cavity site, comprising in combination:

said lasing catheter having an elongated flexible body with a said distal end region;

at least one side port located in said solid distal end region having an aperture;

at least one elongate fiberoptic in said lasing catheter terminating at said aperture in said side aperture for directing a laser beam sent through said fiberoptic at a target site adjacent to said port; said fiberoptic being bent at an angle ranging from about twenty (20) degrees to about ninety (90) degrees from a central axis of said lasing catheter adjacent said side port directed outwardly from said aperture so as to allow delivery of laser energy outwardly from said side port.

2. The lasing catheter in accordance with claim 1 wherein said side port is at least 1 millimeter from said distal end region of said lasing catheter.

3. The lasing catheter in accordance with claim 1 wherein a plurality of fiberoptics are held within said lasing catheter and terminate at said side port.

4. The lasing catheter in accordance with claim 1, further including a flushing channel formed in said lasing catheter; said flushing channel terminating in an outlet port at said side port, adjacent said distal end region of said lasing catheter.

5. The lasing catheter in accordance with claim 4 wherein said outlet port of said flushing channel surrounds a plurality of fiberoptics.

6. The lasing catheter in accordance with claim 4 wherein said outlet port of said flushing channel is surrounded by a plurality of fiberoptics.

7. The lasing catheter in accordance with claim 1 wherein said lasing catheter has an outside diameter ranging from about 1 millimeter to about 3 millimeters.

8. The lasing catheter in accordance with claim 1 wherein said laser beam exiting said at least one fiberoptic exits at a divergence angle which approaches the acceptance angle of said at least one fiberoptic.

9. The lasing catheter in accordance with claim 1 wherein said at least one fiberoptic is comprised of a central core material and at least one layer of cladding material; said at least one layer of cladding material having an index of refraction that is significantly lower than that of said central core material.

10. A lasing catheter in accordance with claim 1 wherein said lasing catheter includes a cap mounted to said distal end region.

11. A lasing catheter in accordance with claim 10 wherein said cap is made of a material that can absorb laser light and generate heat.

12. A lasing catheter in accordance with claim 10 wherein said cap has an inner lining that is made of material that transmits laser energy while providing thermal insulation.

13. A lasing catheter in accordance with claim 10 wherein said cap is removably secured to said lasing catheter.

14. A lasing catheter in accordance with claim 10, further including a thermocouple in contact with said cap to monitoring and controlling temperature of said cap.

15. A lasing catheter in accordance with claim 10, further including a closed loop feedback control system for controlling temperature of said cap.

16. A lasing catheter in accordance with claim 10 wherein said cap includes an inner surface spaced from an outside surface of said distal end region to define a conduit for passage of irrigating fluid during operation of said lasing catheter.

17. A lasing catheter in accordance with claim 1 wherein said bend in said at least one fiberoptic is forty-five (45) degrees from said central axis of said lasing catheter.

18. A lasing catheter in accordance with claim 1 wherein said at least one fiberoptic is selected from suitable materials to produce a high numerical aperture and includes at least one cladding material, to thereby provide said laser beam with an increased launching angle and a maximum limit of its divergence angle.

19. A lasing catheter for laser ablation of human tissue, in a selected body cavity comprising in combination:

said lasing catheter having an elongated flexible body with a solid distal end region;

located in least one laser port at said solid distal end region having an aperture;

at least one elongate fiberoptic in said lasing catheter terminating at said aperture in said laser port for directing a laser beam outwardly through said fiberoptic at a target site near aperture in said laser port; and said fiber optic being adjacent said aperture;

a cap made from a material that can absorb laser light and generate heat mounted to said distal end region covering said laser port so as to absorb all of said laser light from said laser beam.

* * * * *

UNITED STATES PATENT AND TRADEMARK OFFICE
CERTIFICATE OF CORRECTION

PATENT NO. : 5,487,740
DATED : January 30, 1996
INVENTOR(S) : Sulek et al.

It is certified that error appears in the above-indentified patent and that said Letters Patent is hereby corrected as shown below:

Column 4, line 24 "2-2" should be --A-A--; line 26, "3-3" should be --A-A--; line 28, "taken along line 4-4" should be deleted. Column 5, line 10, "2-2" should be --A-A--; line 12, "housing 2" should be --housing 16--; line 13, "tip 1" should be --tip 14--; line 14, "tubing 3" should be --tubing 18--; line 18, delete "20"; line 20, "3-3" should be --A-A--; line 24, "fiberoptic 15" should be --fiberoptic 21--; line 25, "fiberoptic 15" should be --fiberoptic 21--. Column 7, line 31, delete "43"; line 50, "of FIG. 8" should be --of FIG. 5--; line 53, "of FIG. 15" should be --of FIG. 5--. Column 8, line 31, "cap 48" should be --cap 58--; line 44, "said distal" should be --solid distal--; line 48, "side aperture" should be --side port--; line 50, "said port" should be --said aperture--. Column 9, line 32, "cap to" should be --cap for--. Column 10, line 19, "located in" should be --at--; "at" should be --located in--; line 24, "near aperture" should be --near said aperture--.

Signed and Sealed this

Sixth Day of August, 1996

Attest:

BRUCE LEHMAN

*Attesting Officer*    *Commissioner of Patents and Trademarks*